(12) United States Patent
Yang et al.

(10) Patent No.: US 11,415,491 B2
(45) Date of Patent: Aug. 16, 2022

(54) PUMPING MECHANISM FOR GAS SENSORS

(71) Applicant: Apple Inc., Cupertino, CA (US)

(72) Inventors: Henry H. Yang, Los Gatos, CA (US); Roberto M. Ribeiro, San Jose, CA (US)

(73) Assignee: Apple Inc., Cupertino, CA (US)

( * ) Notice: Subject to any disclaimer, the term of this patent is extended or adjusted under 35 U.S.C. 154(b) by 278 days.

(21) Appl. No.: 16/145,054

(22) Filed: Sep. 27, 2018

(65) Prior Publication Data
US 2020/0103318 A1  Apr. 2, 2020

(51) Int. Cl.
*G01N 1/22* (2006.01)
*F04B 45/047* (2006.01)
*G01N 33/00* (2006.01)

(52) U.S. Cl.
CPC ......... *G01N 1/2273* (2013.01); *F04B 45/047* (2013.01); *G01N 33/0027* (2013.01); *G01N 2001/2276* (2013.01)

(58) Field of Classification Search
CPC ............. G01N 1/2273; G01N 33/0027; G01N 1/2276; F04B 45/047
See application file for complete search history.

(56) References Cited

U.S. PATENT DOCUMENTS

| | | | | |
|---|---|---|---|---|
| 5,421,844 A * | 6/1995 | Chiu | ...... | B01D 46/10 96/400 |
| 5,472,032 A * | 12/1995 | Winston | ...... | F04B 43/046 152/415 |
| 5,788,832 A * | 8/1998 | Howard | ...... | G01N 27/404 205/775 |
| 8,196,576 B2 * | 6/2012 | Kriksunov | ...... | A61M 15/0035 128/203.15 |
| 10,156,553 B2 * | 12/2018 | Choi | ...... | G01N 1/2273 |
| 2005/0054905 A1 * | 3/2005 | Corl | ...... | A61B 5/14539 600/309 |
| 2005/0084203 A1 * | 4/2005 | Kane | ...... | B01L 3/50273 385/16 |
| 2008/0154535 A1 * | 6/2008 | Sparks | ...... | G05B 19/0425 702/130 |
| 2011/0309552 A1 * | 12/2011 | Amirouche | ...... | A61M 5/16804 264/331.11 |
| 2014/0134053 A1 * | 5/2014 | Mayer | ...... | G01N 33/0009 422/83 |
| 2014/0326048 A1 * | 11/2014 | Jaffe | ...... | A61B 5/082 73/31.05 |
| 2019/0302073 A1 * | 10/2019 | Mou | ...... | H01L 41/053 |
| 2019/0331582 A1 * | 10/2019 | Mou | ...... | G01N 33/0073 |

FOREIGN PATENT DOCUMENTS

EP          2905673 A2 *  8/2015  ......... G01N 33/0009

* cited by examiner

*Primary Examiner* — Lisa M Caputo
*Assistant Examiner* — Alex T Devito
(74) *Attorney, Agent, or Firm* — BakerHostetler (57) ABSTRACT

A gas-sensing apparatus with gas convection capability includes a gas sensor mounted inside a container, a substrate forming a bottom plate of the container and an actuator. The gas sensor is mounted over a first surface of the substrate internal to the container. The actuator is coupled to a second surface of the substrate external to the container. The actuator can cause convection of a gas within the container by enabling movements of the substrate in response to an activation signal.

20 Claims, 5 Drawing Sheets

PUMPING MECHANISM FOR GAS SENSORS

TECHNICAL FIELD

The present description relates generally to sensor technology, and more particularly, to a pumping mechanism for gas sensors.

BACKGROUND

Portable communication devices (e.g., smart phones and smart watches) are becoming increasingly equipped with environmental sensors such as pressure, temperature and humidity sensors, gas sensors and particulate matter (PM) sensors. For example, a pressure sensor can enable health and fitness features in a smart watch or a smart phone. A measured pressure can then be converted (e.g., by a processor) to other parameters related to pressure, for example, elevation, motion, flow, or other parameters. Pressure sensors can be used to measure pressure in a gas or liquid environment.

Gas sensors may be used in e-nose devices which use various sampling techniques to detect a variety of gas species, for example, oxygen, carbon dioxide ($CO_2$), carbon monoxide (CO), natural gas, ozone, water vapor, toxic gases and other gas species. The gas sample can induce a reversible physical or chemical change in the sensing material of the gas sensor, which can cause a corresponding change in electrical properties such as conductivity of the sensing material. Gas sensors can be fabricated using thick films or thin-film technology. For example, metal oxide sensors such as tin dioxide ($SnO_2$) gas sensors can be built using thick film deposition methods on substrates such as silicon. The sensing properties of metal oxide sensors may be altered by doping. For instance, a $SnO_2$ gas sensing layer may be doped with 1 or 2 percent of cadmium sulphide (CdS). Thin-film gas sensors may have a lower sensitivity compared to thick-film sensors. Selectivity of a gas sensor may be adversely affected by buildup of residual gases around the sensor. There is a need for gas sensors that can prevent buildup of residual gases around the sensor.

BRIEF DESCRIPTION OF THE DRAWINGS

Certain features of the subject technology are set forth in the appended claims. However, for purposes of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute part of the detailed description. The detailed description includes specific details for the purpose of providing a thorough understanding of the subject technology. However, the subject technology is not limited to the specific details set forth herein and may be practiced without one or more of the specific details. In some instances, structures and components are shown in a block diagram form in order to avoid obscuring the concepts of the subject technology.

The subject technology is directed to a gas-sensing apparatus with gas convection capability. The apparatus includes a gas sensor, a substrate and an actuator. The gas sensor is mounted inside a container, and the substrate forms a bottom plate of the container. The actuator is coupled to the substrate and can cause convection of a gas within the container by enabling movements of the substrate in response to an activation signal. The gas sensor is mounted over a first surface of the substrate that is internal to the container, and the actuator is coupled to a second surface of the substrate that is external to the container.

In one or more implementations, the actuator is a piezoelectric actuator or an electromechanical actuator, and the activation signal is an electric voltage that can cause a mechanical motion of the actuator. In other implementations, the actuator can be a thermal bi-stable actuator or a shape memory alloy, and the activation signal is an electric current that can result in resistive heating of the actuator. The apparatus may include a heat-insulating block decoupling the gas sensor from the substrate to prevent unwanted heating of the gas sensor.

In some implementations, the substrate is a flexible membrane, for example, made of a polymer such as polyimide. In one or more implementations, the flexible membrane can have a compliant ring portion that flexibly couples a central portion of the flexible membrane to a surrounding portion. In some implementations, the apparatus includes a springy structure used to flexibly couple the gas sensor to the substrate. The apparatus can further include an air-permeable membrane covering a top opening of the container. The apparatus can be used to detect clogging of pores of the air-permeable membrane by using it to measure a gas concentration inside the container with and without activation of the actuator.

Figure 1A:
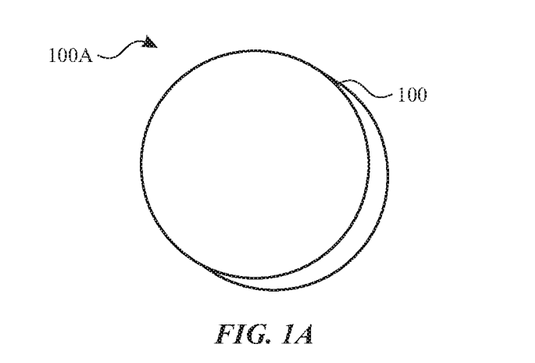
FIGS. 1A through 1C are diagrams illustrating an example of a gas-sensing apparatus and corresponding cross-sectional and top views, in accordance with one or more aspects of the subject technology.
Figure 1B:
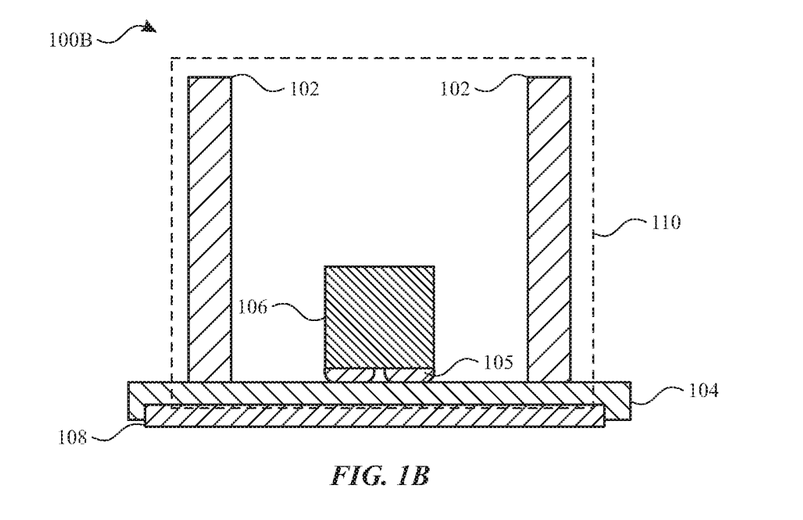
Figure 1C:
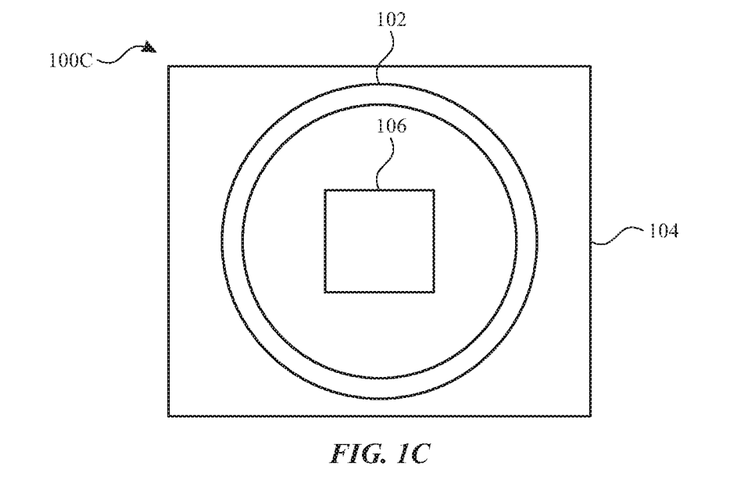

FIGS. 1A through 1C are diagrams illustrating an example of a gas-sensing apparatus 100 and corresponding cross-sectional and top views, in accordance with one or more aspects of the subject technology. FIG. 1A shows a high-level diagram of the gas-sensing apparatus 100, the structural and functional details of which are described herein with respect to various drawings showing different embodiments of the subject technology. The gas-sensing apparatus 100 can be a miniature gas-sensing apparatus suitable for integration with a handheld device, for example, a portable communication device such as a smart phone and/or a smart watch.

FIG. 1B shows a cross-sectional view 100B of the gas-sensing apparatus 100. As shown in the cross-sectional view 100B, the gas-sensing apparatus 100 includes a wall 102 disposed on a substrate 104, forming a container 110. A gas sensor 106 is mounted inside the container 110 over the substrate 104 using, for example, interconnect layers 105 (e.g., solder bumps). In one or more implementations, the gas sensor 106 can be mounted on a semiconductor chip (not shown for simplicity) including electronic circuitry. The gas-sensing apparatus 100 further includes an actuator 108, which is the heart of the current disclosure, as discussed in more detail herein. The gas-sensing apparatus 100 can be a miniature apparatus (e.g., with a few mm dimensions) integratable with a portable communication device, such as a smart phone or a smart watch.

The gas sensor 106 can detect a variety of gas species, for example, oxygen, carbon dioxide ($CO_2$), carbon monoxide (CO), natural gas, ozone, water vapor (e.g., humidity), toxic gases and other gas species. In one or more implementations, the gas sensor 106 can be a miniature gas sensor such as a micro electromechanical system (MEMS) sensor, for example, of a sensor array of an e-noise system. The sensing material of the gas sensor 106 can, for instance, be a conducting polymer, which is deposited as a thick film on a substrate. In some implementations, the substrate can be the substrate 104. The output signal of the sensor 106 is an electrical signal that can be used to identify one or more gases in a gas sample. Interaction of different gases with the gas sensor 106 may change an electrical property of the gas sensor 106, for example, a resistance or a conductance of the gas sensor 106.

For proper functioning of the gas-sensing apparatus 100, there has to be a convection of the gas sample around the gas sensor 106, so that the gas sensor 106 can sense a gas species of interest. The convection prevents buildup of unwanted and/or residual gas species over the gas sensor 106 that can result in affecting the sensitivity and selectivity of the gas sensor 106. The actuator 108 of the subject technology is introduced to solve this problem by generating a convection flow of the air including the gas sample near the sensor 106. The actuator 108 generates the convection flow by inducing mechanical motions of the substrate 104, which can result in a pumping action that generates the convection flow. The substrate 104 can be a flexible substrate made, for example, of a polymer such as polyimide or can have a flexible or compliant portion on which the gas sensor 106 is mounted or formed.

The actuator 108 can be a voltage-activated actuator such as a piezo-electric actuator or an electromechanical actuator, where the activation signal is an electric voltage. Applying the voltage activation signal to the actuator 108, a mechanical motion can be generated that can induce motion such as vibration of the substrate 104, which in turn causes a convention flow of the air including the gas sample near the gas sensor 106. The activation voltage can be within a range of a few millivolts to a few volts, depending on the type of the actuator. Typically, the piezo-electric actuators may work with lower voltages than the electromechanical actuators. In some implementations, the activation signal can be a series of voltage pulses such as a periodic pulse signal that can sequentially (e.g., periodically) change the state of the actuator between off and on states.

In some implementations, the actuator 108 can be a current-activated actuator such as a thermal bi-stable actuator or a shape memory alloy. A thermal bi-stable actuator can be a MEMS actuator that is activated by heat generated by an activation current. The activation current can generate heat in a resistor element of the MEMS actuator. The shape memory alloy is a lightweight alloy made of a solid-state material that can remember its original shape and when deformed, can return to its pre-deformed shape, in response to applied heat. Examples of shape memory alloys include copper-aluminum-nickel, and nickel-titanium (NiTi) alloys, but the shape memory alloys are not limited to these alloys and can also be created by alloying zinc, copper, gold and iron. In some implementations, the heat used for activation of the thermal bi-stable actuator or the shape memory alloy can be generated by the activation current. The generated heat by the activation current for the shape memory alloy is within a range of about 35° C.-45° C., which can bring the shape memory alloy into a hot state. In some implementations, the activation signal can be a series of current pulses such as a periodic current pulse signal that can sequentially (e.g., periodically) change the state of the shape memory alloy between hot and cold states. The activation signal can be generated by an electronic circuit integrated with the gas sensor 106 on the same semiconductor chip or substrate such as a flex substrate. In some implementations, the activation signal can be generated by an electronic circuit or a processor of a host device (e.g., a portable communication device).

FIG. 1C shows a top view 100C of the gas-sensing apparatus 100. In the top view 100C, the wall 102 of the container 110 is shown as a ring and the gas sensor 106 as a square. The top view of the shape of the wall 102 can be a different shape than shown in FIG. 1C, for example, a square shape or other simple shapes.

Figure 2A:
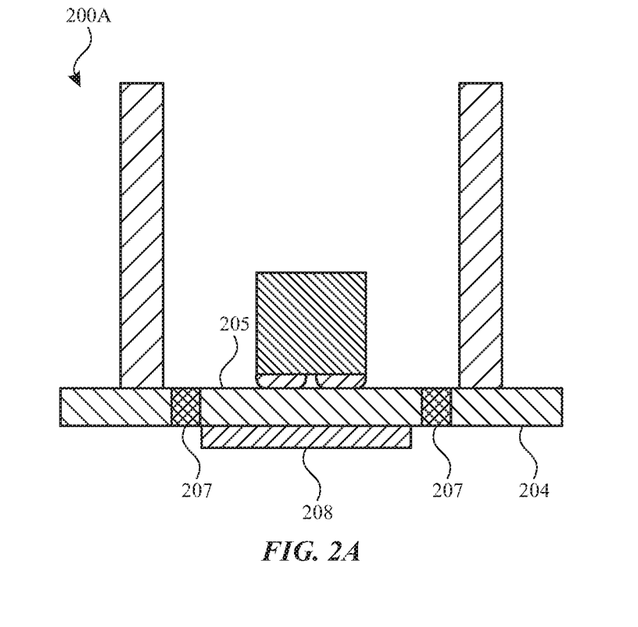
FIGS. 2A through 2C are diagrams illustrating cross-sectional and top views of the example gas-sensing apparatus of FIG. 1A, in accordance with one or more aspects of the subject technology.

FIGS. 2A through 2C are diagrams illustrating cross-sectional and top views of the example gas-sensing apparatus 100 of FIG. 1A, in accordance with one or more aspects of the subject technology. The cross-sectional view 200A of FIG. 2A depicts an embodiment of the gas-sensing apparatus 100, which is similar to the embodiment shown in the cross-sectional view 100B of FIG. 1B, except for a change in the structure of the substrate 104 of FIG. 1B. The substrate 204, replacing the substrate 104 of FIG. 1B, includes a compliant portion (e.g., ring) 115, which allows mechanical motion of a central portion 205 of the substrate 204. The actuator 208 is similar to the actuator 108 of FIG. 1B, but its mechanical motion is applied only to the central portion 205 of the substrate 204.

Figure 2B:
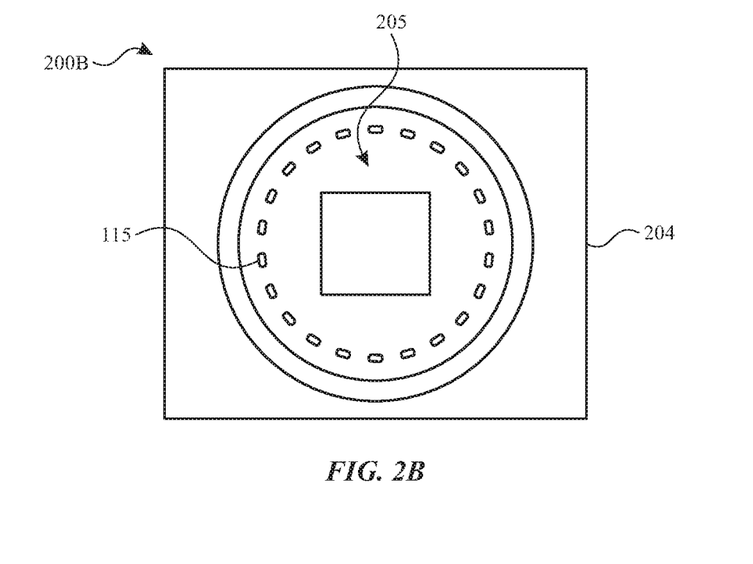

The top view 200B of FIG. 2B is similar to the top view 100C of FIG. 1C, except that it shows the compliant portion (ring) 207, separating the central portion 205 from the rest of the substrate 204. The shape of the top view of the compliant portion (ring) 207 can be a different shape than shown in FIG. 2B, for example, a square shape or other simple shapes.

Figure 2C:
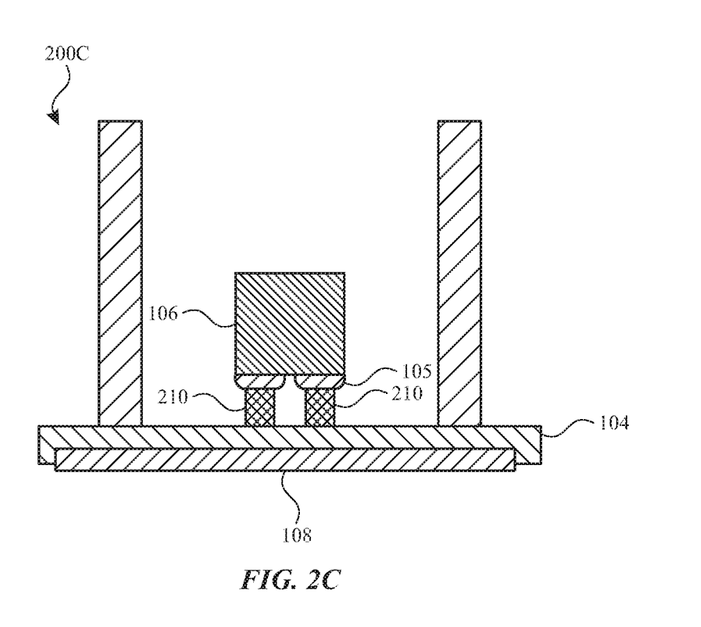

The cross-sectional view 200C of FIG. 2C depicts an embodiment of the gas-sensing apparatus 100, which is similar to the embodiment shown in the cross-sectional view 100B of FIG. 1B, except for a change in mounting of the gas sensor 106 over the substrate 104. In the example embodiment of the gas-sensing apparatus 100 shown in FIG. 2C, the gas sensor 106 is coupled to the substrate 104 via a number (e.g., three or more) of springy structures 210. The springy structures 210 can be actual miniature (about 1 mm in size) springs or made of a compressible material. It is understood that the displacement of the springy structure 210 can be maximized when it is run at a resonance frequency of the springy structure 210. The gas sensor 106 can be attached to the springy structure 210, for example, via interconnect layers 105 or other epoxy layers. The springy structures 210 can be attached to the substrate 104 by using an epoxy layer. In some implementations, the springy structures 210 can be created on the substrate 104 when the substrate is being fabricated.

Figure 3:
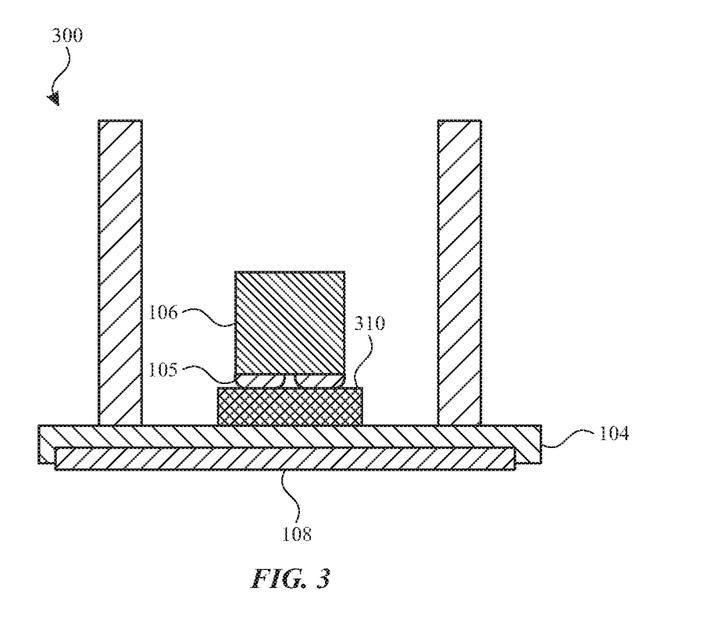
FIG. 3 is a diagram illustrating a cross-sectional view of the example gas-sensing apparatus of FIG. 1A, in accordance with one or more aspects of the subject technology.

FIG. 3 is a diagram illustrating a cross-sectional view 300 of the example gas-sensing apparatus 100 of FIG. 1A, in accordance with one or more aspects of the subject technology. The cross-sectional view 300 of FIG. 3 depicts an embodiment of the gas-sensing apparatus 100, which is similar to the embodiment shown in the cross-sectional view 200C of FIG. 2C, except for a change in mounting of the gas sensor 106 over the substrate 104. In the embodiment of the gas-sensing apparatus 100 shown in the cross-sectional view 300, the coupling of the gas sensor 106 to the substrate 104 is provided by a layer 310, which is a heat-insulating layer, instead of the springy structures 210 of FIG. 2C. The heat-insulating layer 310 can block heat transfer between the actuator 108 and the gas sensor 106, thus preventing the gas sensor 106 from being exposed to temperatures that are not within its operating temperature range. This is particularly important when the actuator 108 is a thermal bi-stable actuator or a shape memory alloy working with heat generating activation signals. The gas sensor 106 can be mounted over the heat insulating layer 310 via the interconnect layers 105 or any other attachment layers such as a suitable epoxy. In some implementations, the heat-insulating layer 310 can be created on the substrate 104 when the substrate is being fabricated.

Figure 4:
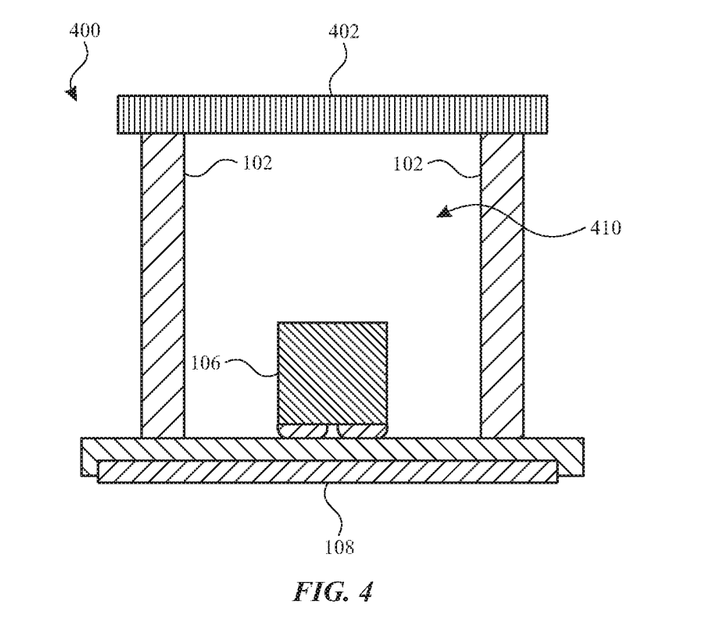
FIG. 4 is a diagram illustrating a cross-sectional view of the example gas-sensing apparatus of FIG. 1A, in accordance with one or more aspects of the subject technology.

FIG. 4 is a diagram illustrating a cross-sectional view 400 of the example gas-sensing apparatus 100 of FIG. 1A, in accordance with one or more aspects of the subject technology. The cross-sectional view 400 of FIG. 4 depicts an embodiment of the gas-sensing apparatus 100, which is similar to the embodiment shown in the cross-sectional view 100B of FIG. 1B, except for the addition of a membrane 402 covering a top opening of the gas-sensing apparatus 100, which was not used in the embodiment shown in the cross-sectional view 100B. In one or more implementations, the membrane 402 can be an air-permeable membrane that can allow air and/or gas circulation between a cavity 410 of the gas-sensing apparatus 100 and the surrounding environment. When some pores of the membrane 402 are clogged by particulate matters, the operation of the gas-sensing apparatus 100 can be affected as the response time of the gas sensor 106 may change. The response time can be compared with the initial (e.g., factory) response time of the gas sensor to detect whether the pores of the membrane 402 are clogged (e.g., partially). In one or more implementations, measuring concentrations of an environmental gas (e.g., humidity) with and without activation of the actuator 108 and comparing the results can reveal if the pores of the membrane 402 are clogged. For equal measurement times, with and without activation of the actuator 108, the measured concentration of the environmental gas is expected to be less when the pores of the membrane 402 are clogged.

Figure 5:
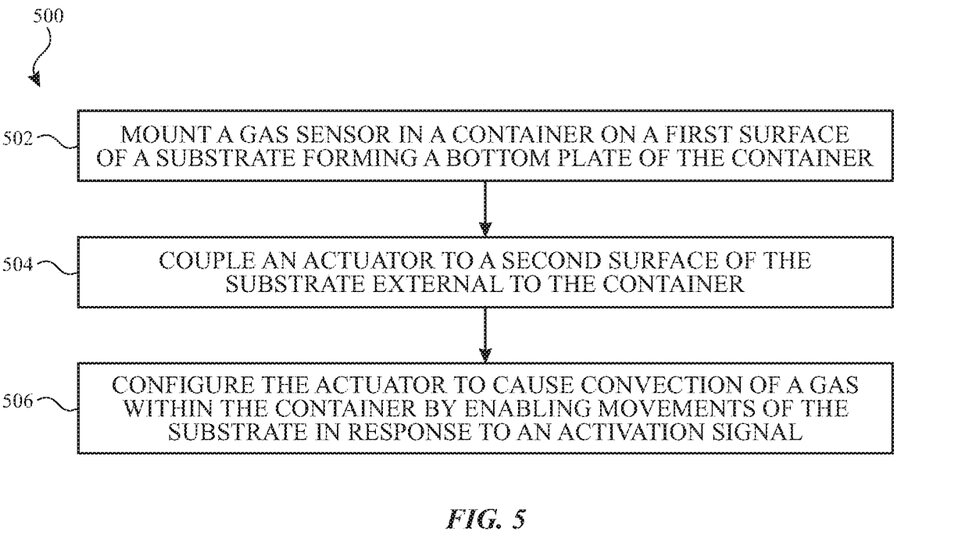
FIG. 5 is a flow diagram illustrating an example method for providing a gas sensing apparatus, in accordance with one or more aspects of the subject technology.

FIG. 5 is a flow diagram illustrating an example method 500 for providing a gas-sensing apparatus, in accordance with one or more aspects of the subject technology. The method 500 includes mounting a gas sensor (e.g., 106 of FIG. 1B) in a container (e.g., 110 of FIG. 1B) on a first surface (e.g., top surface) of a substrate (e.g., 104 of FIG. 1B) forming a bottom plate of the container (502). The method 500 further includes coupling an actuator (e.g., 108 of FIG. 1B) to a second surface (e.g., bottom surface) of the substrate external to the container (504). The actuator is configured to cause convection of a gas within the container by enabling movements of the substrate in response to an activation signal (506).

Figure 6:
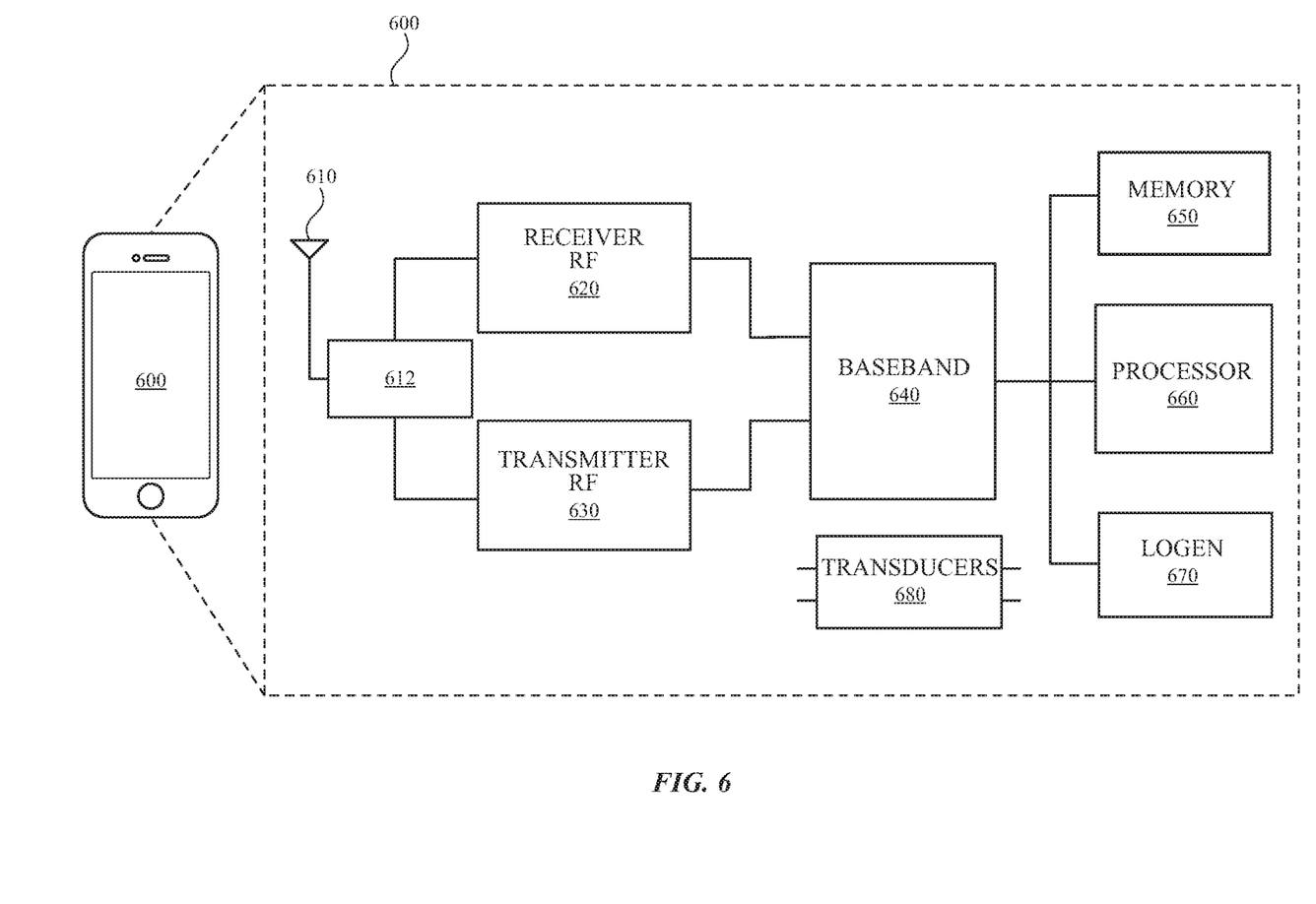
FIG. 6 is a block diagram illustrating a wireless communication device, within which one or more aspects of the subject technology can be implemented.

FIG. 6 is a block diagram illustrating a wireless communication device, within which one or more aspects of the subject technology can be implemented. In one or more implementations, the wireless communication device 600 can be a smart phone or a smart watch that hosts an apparatus of the subject technology including a sensor (e.g., a gas sensor) and an activation layer capable of pumping the gas samples near the gas sensor. The wireless communication device 600 may comprise a radio-frequency (RF) antenna 610, a receiver 620, a transmitter 630, a baseband processing module 640, a memory 650, a processor 660, a local oscillator generator (LOGEN) 670, and one or more transducers 680. In various embodiments of the subject technology, one or more of the blocks represented in FIG. 6 may be integrated on one or more semiconductor substrates. For example, the blocks 620-670 may be realized in a single chip or a single system on a chip, or may be realized in a multi-chip chipset.

The receiver 620 may comprise suitable logic circuitry and/or code that may be operable to receive and process signals from the RF antenna 610. The receiver 620 may, for example, be operable to amplify and/or down-convert received wireless signals. In various embodiments of the subject technology, the receiver 620 may be operable to cancel noise in received signals and may be linear over a wide range of frequencies. In this manner, the receiver 620 may be suitable for receiving signals in accordance with a variety of wireless standards, Wi-Fi, WiMAX, Bluetooth, and various cellular standards. In various embodiments of the subject technology, the receiver 620 may not require any surface acoustic wave (SAW) filters and few or no off-chip discrete components such as large capacitors and inductors.

The transmitter 630 may comprise suitable logic circuitry and/or code that may be operable to process and transmit signals from the RF antenna 610. The transmitter 630 may, for example, be operable to up-convert baseband signals to RF signals and amplify RF signals. In various embodiments of the subject technology, the transmitter 630 may be operable to up-convert and amplify baseband signals processed in accordance with a variety of wireless standards. Examples of such standards may include Wi-Fi, WiMAX, Bluetooth, and various cellular standards. In various embodiments of the subject technology, the transmitter 630 may be operable to provide signals for further amplification by one or more power amplifiers.

The duplexer 612 may provide isolation in the transmit band to avoid saturation of the receiver 620 or damaging parts of the receiver 620, and to relax one or more design requirements of the receiver 620. Furthermore, the duplexer 612 may attenuate the noise in the receive band. The duplexer may be operable in multiple frequency bands of various wireless standards.

The baseband processing module 640 may comprise suitable logic, circuitry, interfaces, and/or code that may be operable to perform processing of baseband signals. The baseband processing module 640 may, for example, analyze received signals and generate control and/or feedback signals for configuring various components of the wireless communication device 600, such as the receiver 620. The baseband processing module 640 may be operable to encode, decode, transcode, modulate, demodulate, encrypt, decrypt, scramble, descramble, and/or otherwise process data in accordance with one or more wireless standards.

The processor 660 may comprise suitable logic, circuitry, and/or code that may enable processing data and/or controlling operations of the wireless communication device 600. In this regard, the processor 660 may be enabled to provide control signals to various other portions of the wireless communication device 600. The processor 660 may also control transfer of data between various portions of the wireless communication device 600. Additionally, the processor 660 may enable implementation of an operating system or otherwise execute code to manage operations of the wireless communication device 600. In one or more implementations, the processor 660 can be used to send commands to the actuator 108 of FIG. 1B to induce mechanical motion of the substrate 104 that results in convection of gas around the gas sensor 106 of FIG. 1B. In one or more implementations, the processor 660 can process signals received from the gas sensor (e.g., 106 of FIG. 1B) to detect presence, type and/or concentration of the gas inside the cavity 410 of the gas-sensing apparatus of FIG. 4.

The memory 650 may comprise suitable logic, circuitry, and/or code that may enable storage of various types of information such as received data, generated data, code, and/or configuration information. The memory 650 may comprise, for example, RAM, ROM, flash, and/or magnetic storage. In various embodiments of the subject technology, information stored in the memory 650 may be utilized for configuring the receiver 620 and/or the baseband processing module 640. In some implementations, the memory 650 may store information regarding the type of the gas and/or the concentration or other information related to the gas inside the cavity 410 of the gas-sensing apparatus of FIG. 4.

The local-oscillator generator (LOGEN) 670 may comprise suitable logic, circuitry, interfaces, and/or code that may be operable to generate one or more oscillating signals of one or more frequencies. The LOGEN 670 may be operable to generate digital and/or analog signals. In this manner, the LOGEN 670 may be operable to generate one or more clock signals and/or sinusoidal signals. Characteristics of the oscillating signals such as the frequency and duty cycle may be determined based on one or more control signals from, for example, the processor 660 and/or the baseband processing module 640.

In operation, the processor 660 may configure the various components of the wireless communication device 600 based on a wireless standard according to which it is desired to receive signals. Wireless signals may be received via the RF antenna 610, amplified, and down-converted by the receiver 620. The baseband processing module 640 may perform noise estimation and/or noise cancellation, decoding, and/or demodulation of the baseband signals. In this manner, information in the received signal may be recovered and utilized appropriately. For example, the information may be audio and/or video to be presented to a user of the wireless communication device, data to be stored to the memory 650, and/or information affecting and/or enabling operation of the wireless communication device 600. The baseband processing module 640 may modulate, encode, and perform other processing on audio, video, and/or control signals to be transmitted by the transmitter 630 in accordance with various wireless standards.

In one or more implementations, the transducers 680 may include a miniature sensor such as the MEMS sensor (e.g., a gas sensor) of the subject technology, for example, as shown in FIG. 1A and described above with respect to FIGS. 1B through 1C, 2A through 2C, 3 and 4. The gas-sensing apparatus 100 of the subject technology can be readily integrated into the communication device 600, in particular, when the communication device 600 is a smart mobile phone or a smart watch.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter genders (e.g., her and its) and vice versa. Headings and subheadings, if any, are used for convenience only and do not limit the subject disclosure.

The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

The word "example" is used herein to mean "serving as an example or illustration." Any aspect or design described herein as "example" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A gas-sensing apparatus with gas convection capability, the apparatus comprising:
   a housing filled with air and gas;
   a gas sensor entirely enclosed by the housing;
   a substrate configured to form a bottom plate of the housing of the apparatus; and
   an actuator coupled to the substrate and configured to induce mechanical motions of the substrate in response to an activation signal to generate a convection flow of the air and the gas within the housing,
      wherein the actuator is coupled to a surface of the substrate external to the housing, and wherein the substrate forming the bottom plate of the housing includes a central solid portion bonded via interconnect layers to the gas sensor and a compliant ring portion that allows mechanical motion of the central solid portion.

2. The apparatus of claim 1, wherein the actuator comprises one of a piezo-electric actuator or an electromechanical actuator, and wherein the activation signal comprises an electric voltage resulting in the mechanical motions.

3. The apparatus of claim 1, wherein the actuator comprises one of a thermal bi-stable actuator or a shape memory alloy, wherein the activation signal comprises an electric current resulting in a resistive heat generation.

4. The apparatus of claim 3, further comprising a heat insulating block decoupling the gas sensor from the substrate.

5. The apparatus of claim 1, wherein the substrate comprises a flexible membrane, and wherein the flexible membrane comprises polyimide.

6. The apparatus of claim 5, wherein the compliant ring portion is configured to flexibly couple the central solid portion of the flexible membrane to a surrounding solid portion of the substrate.

7. The apparatus of claim 1, further comprising a springy structure used to flexibly couple the gas sensor to the substrate.

8. The apparatus of claim 1, further comprising an air-permeable membrane covering a top opening of the housing.

9. The apparatus of claim 8, wherein the apparatus is configured to detect clogging of pores of the air-permeable membrane when used to measure gas concentration with and without activation of the actuator.

10. A communication device comprising:
a processor; and
a gas-sensing device with gas convection capability comprising:
    a housing filled with air and gas and including a substrate configured to form a bottom plate of the housing;
    a gas sensor entirely enclosed by the housing; and
    an actuator coupled to an external surface of the substrate and configured to induce mechanical motions of the substrate in response to an activation signal from the processor to generate a convection flow of air including a gas within the housing, wherein the substrate forming the bottom plate of the housing includes a central solid portion bonded via interconnect layers to the gas sensor and a compliant ring portion that allows mechanical motion of the central solid portion.

11. The communication device of claim 10, wherein the gas sensor comprises a micro-electromechanical system (MEMS) pressure sensor disposed on a semiconductor chip that is placed on the substrate.

12. The communication device of claim 10, wherein the actuator is coupled to a surface of the substrate external to the housing.

13. The communication device of claim 10, wherein the activation signal comprises an electric voltage, and wherein the actuator comprises one of a piezo-electric actuator or an electromechanical actuator configured to generate mechanical motion induced by the electric voltage.

14. The communication device of claim 10, wherein the activation signal comprises an electric current, and wherein the actuator comprises one of a thermal hi-stable actuator or a shape memory alloy configured to generate mechanical motion induced by a resistive heat generated by the electric current.

15. The communication device of claim 10, wherein the substrate comprises a flexible membrane including polyimide, and wherein the gas-sensing device further comprises a heat-insulating block decoupling the gas sensor from the substrate.

16. The communication device of claim 15, wherein the compliant ring portion is configured to flexibly couple the central solid portion of the flexible membrane to a surrounding solid portion of the substrate, and wherein the gas-sensing device further comprises a springy structure used to flexibly couple the gas sensor to the substrate.

17. The communication device of claim 15, wherein the gas-sensing device further comprises an air-permeable membrane covering a top opening of the housing, wherein the processor is configured to detect a clogging of pores of the air-permeable membrane, when the gas sensing device is used to measure gas concentration, by turning activation of the actuator on and off.

18. An apparatus for venting a gas sensor, the apparatus comprising:
    a housing filled with air and a gas;
    a substrate configured to form a bottom plate of the housing;
    an actuator coupled to the substrate and configured to induce mechanical motions of the substrate in response to an activation signal; and
    a gas sensor entirely enclosed by the housing,
    wherein the substrate is made of a central solid portion bonded to the gas sensor via interconnect layers and a compliant ring portion that allows mechanical motion of the central solid portion, and wherein the mechanical motion of the central solid portion is capable of inducing convection flow of the air and the gas within the housing.

19. The apparatus of claim 18, wherein the actuator is coupled to a surface of the substrate external to the housing, and wherein the actuator comprises one of a piezo-electric actuator, an electromechanical actuator, a thermal bi-stable actuator or a shape memory alloy.

20. The apparatus of claim 18, wherein the activation signal comprises an electric voltage resulting in the mechanical motions of the actuator or an electric current resulting in a resistive heat generation.

* * * * *

UNITED STATES PATENT AND TRADEMARK OFFICE
CERTIFICATE OF CORRECTION

PATENT NO. : 11,415,491 B2
APPLICATION NO. : 16/145054
DATED : August 16, 2022
INVENTOR(S) : Henry H. Yang et al.

It is certified that error appears in the above-identified patent and that said Letters Patent is hereby corrected as shown below:

In the Claims

Column 10, Line 8 (Claim 14): "hi-stable" should read --bi-stable--.

Signed and Sealed this
Thirtieth Day of April, 2024

Katherine Kelly Vidal
*Director of the United States Patent and Trademark Office*